(12) United States Patent
Mariani, Jr.

(10) Patent No.: US 6,488,498 B1
(45) Date of Patent: Dec. 3, 2002

(54) ELASTIC ORTHODONTIC COMPONENT

(76) Inventor: Richard C. Mariani, Jr., 7600 SW. 57th Ave., South Miami, FL (US) 33143

(*) Notice: Subject to any disclaimer, the term of this patent is extended or adjusted under 35 U.S.C. 154(b) by 0 days.

(21) Appl. No.: 09/653,674

(22) Filed: Sep. 1, 2000

(51) Int. Cl.[7] .................................................. A61C 7/00
(52) U.S. Cl. .......................................... 433/11; 433/18
(58) Field of Search ............................... 433/11, 18, 19, 433/7, 22

(56) References Cited

U.S. PATENT DOCUMENTS

| | | | | |
|---|---|---|---|---|
| 3,530,583 A | * | 9/1970 | Klein et al. | 433/11 |
| 4,382,782 A | * | 5/1983 | Klein et al. | 433/18 |
| 5,897,313 A | * | 4/1999 | Cleary et al. | 433/19 |

* cited by examiner

Primary Examiner—John J. Wilson
Assistant Examiner—Melba Bumgarner

(74) Attorney, Agent, or Firm—Lott & Friedland, P.A.

(57) ABSTRACT

An orthodontic component structured to be mounted within a patients mouth in interconnection relation to spaced apart conventional or customized orthodontic appliances so as to exert a predetermined and pre-directed force on the interconnected orthodontic appliances as well as the teeth to which such appliances are attached. The orthodontic component of the present invention includes a module formed of a elastomeric material having sufficient elastic characteristics to exert the aforementioned force when stretched or expanded into interconnecting relation with the spaced apart appliances. The module comprises a unitary or a one piece construction having an elongated, normally linear configuration and terminating at oppositely disposed ends. Each of said ends comprises an attachment assembly configured to engage the spaced apart orthodontic appliances and be attached thereto in a manner which defines a stable or lasting connection and thereby facilitate removal from its operative position, only by an orthodontist or other trained dental professional.

19 Claims, 2 Drawing Sheets

ELASTIC ORTHODONTIC COMPONENT

BACKGROUND OF THE INVENTION

1. Field of the Invention

The present invention relates to an orthodontic component in the form of an elastomeric module of substantially unitary or one piece construction and having sufficient, predetermined elastic characteristics to be stretched or expanded between spaced apart orthodontic appliances such as, but not limited to, th archwires or brackets attached to the teeth of a patient, and thereby exert a pre-directed force on the interconnected appliances for purpose of properly orienting or positioning malaligned teeth.

2. Description of the Related Art

Orthodontics is a specialty within the field of the dentistry which is distinctive for its innovative design and utilization of a wide variety of dental or, more specifically, orthodontic appliances. Such appliances are utilized by being arranged or mounted within in a patient's mouth in a manner which facilitates the proper positioning of malaligned teeth. In attempting to accomplish such proper positioning, pre-directed forces are applied to the various teeth in order to gradually adjust their orientation and/or position, as desired, over a relatively extended period of time. Although numerous devices and techniques are used for generating the necessary forces and applying them to the teeth, perhaps the most common system currently in use comprises the utilization of an archwire or one or more segmented archwires. The archwire extends arcuately along predetermined teeth in the patient's mouth. Such archwires or archwire segments are secured to the teeth by orthodontic brackets physically mounted on an exposed surface of the individual teeth by conventional means. Such orthodontic brackets normally include one or more slots for receiving and supporting the archwire which is then ligated into receiving portions or slots formed in the brackets.

In addition to the above the aforementioned brackets also include projections or wings which allow for the attachment or interconnection of elastic, force exerting modules. Such elastic modules are conventionally defined by one or more elongated orthodontic chains which are formed of an elastic material and comprise a plurality of integrally connected O-rings secured in spaced relation to one another along the length of the orthodontic chain or chain segment. Such conventional orthodontic chains are operatively applied or positioned by extending the chains between the various brackets attached to spaced apart teeth. More specifically, each of the chains or chain segments, due to the elastic nature of the material from which they are formed, are interconnected to the appliances and extend over a predetermined expanse. Once properly installed or applied, a pre-directed force is exerted on the interconnected brackets or other orthodontic appliances. The exerted force is transferred to the teeth for purposes of accomplishing the aforementioned re-positioning or re-alignment of the teeth as desired.

In addition to the utilization of the elastic chain segments, as set forth above, individual O-ring ties may also be secured to at least minimally spaced apart orthodontic appliances, so as to exert a pre-directed force thereon. Therefore, specialists in the field of orthodontics have a wide variety of different elastic chains, individual elastic ties and other elastic components, specifically designed to exert a pre-directed force on interconnected appliances at there disposable. However, despite the wide spread use of such elastic components, there still exists long recognized and significant disadvantages and problems with their use. Problems existing with conventional elastic components of the type described are even more pronounced when considering the innovative nature of the orthodontist in developing new orthodontic techniques and applications in which elastic components can be used.

Other potentially problematic conditions, in addition to those set forth above, include corrective applications, wherein orthodontic appliances and elastic material components are generally required to be kept in a patient's mouth for a relatively long period of time so as to exert a continuous and adequate amount of force on the various interconnected appliances secured by such elastic components. As such, any orthodontic component remaining in the mouth of a patient should be specifically structured, dimensioned and configured to avoid, as much as possible, any discomfort to the wearer. Also structuring of such orthodontic components, including elastic ties or like structures, should not be capable of being easily removed, particularly by the patient. Premature removal, particularly of the elastic material ties or components, is a relatively frequent occurrence due in part to the fact that the existence of orthodontic devices, components and/or appliances, by their very nature, can be an uncomfortable and unpleasant experience. Accordingly, there should always be an effort to design and apply any orthodontic appliance, including but not limited to elastic components or ties, in a manner which minimizes any potential discomfort to the patient. Designing of the various components in the manner set forth above will tend to minimize attempted self adjustments by a patient and/or the undesirable practice of removing the various elastic material ties, without the knowledge or consent of the orthodontist.

Despite the existence of problems of the type set forth herein, there has been relatively few attempts to modify or structurally improve the elastic components currently known or available. Therefore, based on the above, there is a need in the field of dentistry and particularly in the specialty of orthodontics for an improved orthodontic component preferably defined by an elastic module which overcomes the problems and disadvantages associated with known elastic material components and which includes an uncomplicated structural designs. Such a preferred elastic component, while being particularly adaptable for use in the correction for certain orthodontic conditions, should demonstrate sufficient structural versatility to be applied in a wide variety of different applications, which require pre-directed forces to be accurately applied for the correction of such a condition. In addition, such an improved elastic module or like orthodontic component should be capable of demonstrating a sufficient versatility to allow its use in a wide variety of applications, thereby improving its appeal to orthodontic specialists, which are innovative by their very nature.

SUMMARY OF THE INVENTION

The present invention relates to an orthodontic component preferably in the form of an elongated, elastomeric material module integrally formed into a substantially unitary, one piece construction. The orthodontic component, and more specifically the elastic module, is designed to be disposed within a patients mouth in interconnected engagement between spaced apart conventional and/or customized orthodontic appliances, in order that a pre-directed force is exerted on and between the interconnected orthodontic appliances. The pre-directed forces are thereby also exerted on the teeth to which the appliances are secured.

A structural feature of the elastic module of the present invention is the inclusion of attachment assemblies thereon, which facilitate the establishment and maintenance of lasting or stable connections with the interconnected orthodontic appliances. For purposes of clarity the terms "stable" and/or "lasting" are meant to include a connection, attachment or mounting, which is resistant to change or repositioning, at least to the extent that removal by the patient, as is possible and prevalent with conventional elastic tie members, is prohibited or significantly restricted. To the contrary the design and structure of the elastic module of the present invention provides for its lasting attachment or connection of in its intended, operative position for extended periods. Further, removal or repositioning of the elastic module is intended to be accomplished only by the orthodontist or other appropriately trained medical/dental personnel.

Additional structural features of the present invention comprise material from which the module is formed having sufficient elastic characteristics to exert the proper force, when stretched or expanded into its operative, interconnecting position, between the aforementioned orthodontic appliances. Due to the elasticity of the material from which the module is formed, it will normally assume a generally linear configuration, except when disposed into its operative, force exerting position or when it is otherwise manipulated or oriented into a distorted position.

The two opposite ends defining the extremities of the elongated elastic module each include one of the aforementioned attachment assemblies mounted thereon and/or attached thereto. Each attachment assembly includes a first or connecting portion, preferably formed from the elastomeric material from which the remainder of the module is formed. This connecting portion of each attachment assembly also includes an aperture extending there through and also through or adjacent to a corresponding one of the ends of the module. A second or contact portion of each attachment assembly is defined by a sleeve or tubular component having opposite open ends and a hollow interior. This contact portion is disposed in an inserted, fixed position within the aperture of each of the first, connecting portions of the attachment assembly and is dimensioned to overly and cover the inner surface of the connecting portion in contiguous relation to the circumference of the aperture. In relative terms, the first portion may be considered the connecting portion of each of the attachment assemblies and the second portion may be considered the contact portion, as set forth above. Accordingly, the contact portion is formed from a hard, substantially rigid material which is disposed and dimensioned to engage the orthodontic appliance on which the elastic module is mounted. The contact portion is therefore formed from a durable material, which is substantially harder and more rigid than the elastomeric material from which the module and connecting portions of the attachment assemblies are formed. As a result, the aforementioned stable or lasting connection of the elastic module between the interconnected orthodontic appliances, which may include brackets, archwires or like structures, is thereby accomplished. However, because a vast majority of the module is integrally formed from an elastomeric material, significantly greater comfort is provided to the patient along with elimination or significant reduction in the possibility of the module inadvertently damaging the soft tissue portions of the patient's mouth.

Due to the fact that the elastic module of the orthodontic component of the present invention is specifically intended to be used within a patients mouth for extended periods, both the elastic material from which the module is formed and the hard and/or preferably metallic material from which the contact portion is formed is medically safe and non-reactive to the patient. Also, it is emphasized that the un-complicated, durable and consistently performing structure and design of the elastic module of the present invention greatly enhances its use and diversity of application as it is operatively positioned in interconnecting or otherwise in cooperative attachment to conventional or customized brackets archwires or other orthodontic appliances. This feature of enhanced versatility is particularly appealing to the specialized field of orthodontics in that practitioners within this field frequently demonstrate a considerable degree of innovative adaptation in solving the numerous problems associated with malaligned teeth or other conditions occurring in the practice of orthodontics. Therefore, while the elastic module of the present invention is particularly adaptable for the correction of overbite and underbite problems, it is particularly adaptable to a variety of other problematic situations which the orthodontist encounters on a daily basis.

These and other objects, features and advantages of the present invention will become more clear when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

As shown in the accompanying Figures, the present invention is directed to an orthodontic component generally indicated as 10 comprising a module 12 integrally formed into a substantially unitary or one piece construction from an elastomeric material. The elastic module 12 includes oppositely disposed ends 14 and 16 each preferably being equivalently structured and correspondingly dimensioned and defining opposite extremities of an interconnecting segment 18. The interconnecting segment 18 as well as the opposite ends 14 and 16 are integrally formed of the same elastomeric material which has sufficient elastic characteristics to exert an adequate or applicable amount of force, when the module 12 is expanded or stretched into its operative position. As will be explained in greater detail hereinafter, particularly with regard to FIGS. 7 and 8, the operative position of the elastic module 12 is at least partially defined by it being stretched or expanded into interconnecting relation between brackets, archwires or other appropriate orthodontic appliances. The referred to appliances may comprise either conventional or customized brackets, archwires or like structures, dependent on the particular application for which such orthodontic appliances are utilized.

While the length of the elastic module 12 may assume a convenient or recognized standard length acceptable for a variety of orthodontic applications, it may also be provided in a variety of different lengths each assuming an equivalent structure, intended to be encompassed within the spirit and scope of the present invention, regardless of its length. Also, while the opposite ends 14 and 16 are preferably formed to have the same dimension and configuration, a variance between the size, shape, and other structural features of these ends is contemplated to be within the spirit and scope of the present invention.

Figure 1:
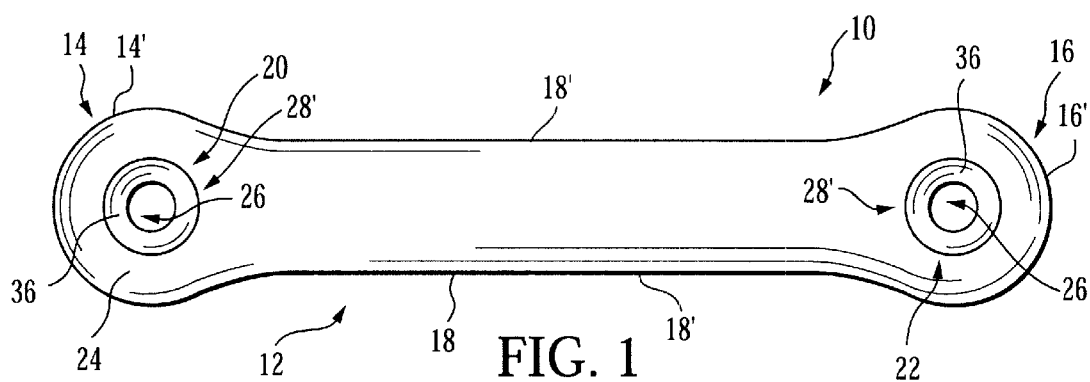
FIG. 1 is a front plan view of the elastic module comprising the orthodontic component of the present invention.
Figure 2:
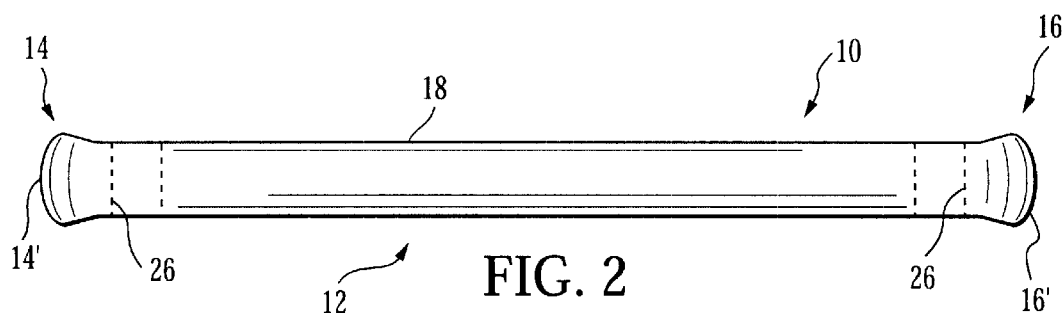
FIG. 2 is a side view in partial phantom of the embodiment of FIG. 1.

With primary reference to FIGS. 1 and 2, the interconnecting segment 18 preferably includes a substantially uniform cross section along at least a majority of a portion of its length extending between the opposite ends 14 and 16. Also, the nature of the elastomeric material from which the module 12 is formed is such that the interconnecting segment 18 will normally assume a generally linear configuration unless it is otherwise manipulated or oriented so as to be distorted in other than a linear configuration. Also while the opposite ends 14 and 16 have a somewhat laterally extended configuration as well as a curved periphery as at 14' and 16', it is emphasized that each of the ends 14 and 16 may have other than a curved peripheral configuration 14' and 16' and may have its lateral borders disposed in co-extensive relation with the longitudinal sides 18' of the intermediate segment 18.

Another structural feature of the present invention comprises the inclusion of two attachment assemblies 20 and 22 formed on and at least partially defining the different ends 14 and 16 of the elastic module 12. In a preferred embodiment, each of the attachment assemblies 20 and 22 are substantially equivalently structured and correspondingly dimensioned. However, the present invention further contemplates the structuring of the attachment assemblies 20 and 22 to include at least minimally different dimensions and at least partially varying configuration, while operating to facilitate a lasting or stable connection with conventional or customized orthodontic appliances of the type described in more detail with reference to FIGS. 7 and 8. Accordingly, a first or connecting portion of each of the attachment assemblies 20 and 22 is indicated as 24 and is integrally formed with the intermediate segment 18 and the rest of the module 12 from the same elastomeric material. Moreover, the first or connecting portion 24 of each of the attachment assemblies 20 and 22 includes an aperture 26 extending through the corresponding ends 14 and 16. Each of the apertures 26 is spaced inwardly from the peripheral surfaces 14' and 16' of the respective ends 14 and 16, such that the first or connecting portion 24 of each of the attachment assemblies 20 and 22 are disposed in at least partially surrounding or enclosing relation to the aperture 26.

Figure 3:
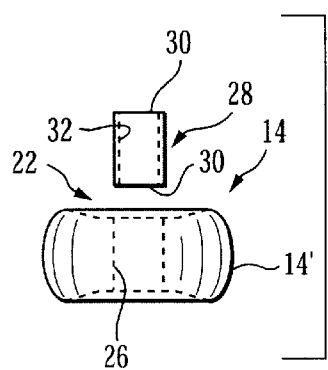
FIG. 3 is an end view in partially exploded form of one embodiment an attachment assembly associated with may be associated with each end of the elastic module of the embodiments of FIGS. 1 and 2.
Figure 4:
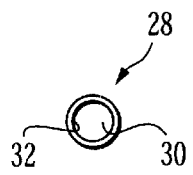
FIG. 4 is a detailed view of a portion of the embodiment of FIG. 3.

In order to facilitate a durable and stable or lasting connection, as set forth above, each of the attachment assemblies 20 and 22 includes a second portion, which may be referred to as a contact portion and is generally indicated as 28 in the embodiment of FIGS. 3 and 4. Contact portion 28 includes a tubular or sleeve-like configuration which includes opposite open ends 30 and a continuous cylindrical sidewall 32. The dimension of the contact portion 28 is such as to be inserted within the aperture 26 of each of the attachment assemblies 20 and 22 so as to be disposed substantially contiguous with the outer circumference of the aperture 26. The contact portion 28 is further dimensioned and configured to be disposed in overlying relation to the inner surface of the connecting portion 24, which defines the peripheral boundaries of the aperture 26.

Figure 5:
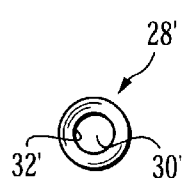
FIG. 5 is an end view of another embodiment of a portion of the attachment assembly which may be utilized in the embodiment of FIGS. 1 and 2.
Figure 6:
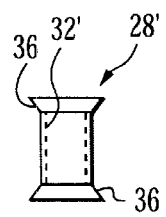
FIG. 6 is a side view of the embodiment of FIG. 5.

In the embodiment of FIGS. 3 and 4, the contact portion 28 has a somewhat straight line configuration and a length substantially corresponding to the longitudinal dimension of the aperture 26 in which it is inserted and to which it is fixedly secured. Another structural variation or embodiment of the contact portion is indicated as 28' in FIGS. 5 and 6. In this embodiment, the contact portion 28' includes a closed or continuous cylindrical sidewall 32', as well as oppositely disposed open ends 30'. However, the embodiment of FIGS. 5 and 6 differs from the embodiment of the contact portion of FIGS. 3 and 4 in that the peripheral edge or boundary of each of the open ends 30' is flared outwardly as at 36. This configuration of the contact portion 28' serves to overly and somewhat protectively cover adjacent, at least partially enclosed surfaces of the first connecting portion 24, defining and/or disposed contiguous or adjacent to the periphery of the aperture 26.

Figure 7:
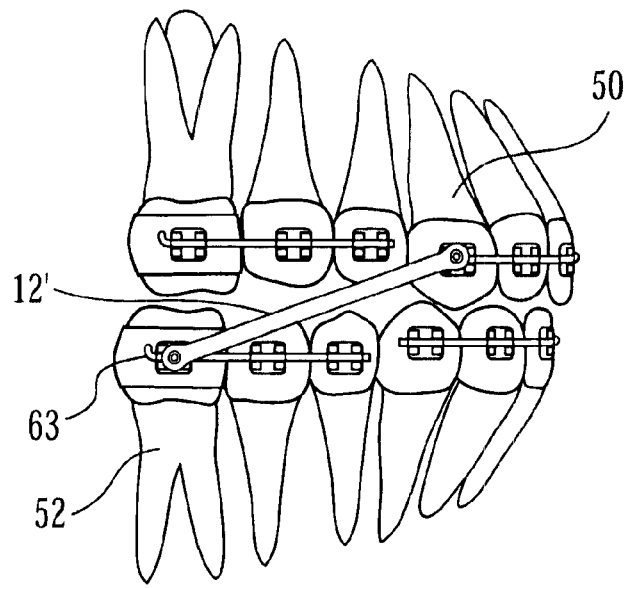
FIG. 7 is a side, partially schematic view of the elastic module of the embodiment of FIGS. 1 and 2 disposed in an operative position intended to correct an overbite condition.
Figure 8:
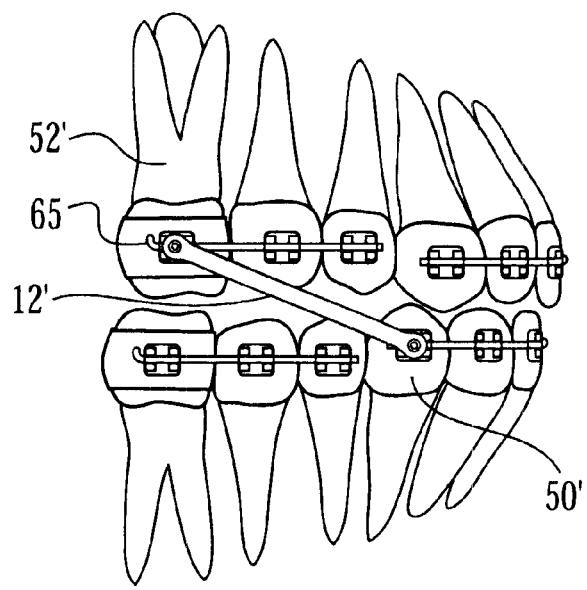
FIG. 8 is a side partially schematic view of the elastic module of the embodiment of FIGS. 1 and 2 shown in a different operative position intended to correct an underbite condition.

As emphasized above the elastic module 12 of the present invention may be used for a variety of different applications and the correcting of numerous conditions, wherein customized or conventional orthodontic appliances may be utilized. With reference to FIGS. 7 and 8, one preferred application in which the elastic module 12 may be utilized is represented in FIG. 7. More specifically, the module schematically represented as 12' has one end 14 or 16 connected to a bracket, archwire or other appropriate orthodontic appliance which is secured to an upper canine tooth 50. The opposite end of the schematically represented elastic module 12' is connected to an orthodontic appliance, such as a bracket, archwire, etc, mounted on a lower molar 52. Accordingly, a force is exerted between the upper canine 50 and the lower molar 52, in an attempt to correct what is known as an overbite condition. Somewhat similarly, the schematically represented elastic module 12' may also be used to correct an underbite condition by establishing a lasting connection between one of the ends 14 or 16 to a lower canine 50' and the other of the ends to the upper molar 52'. Sufficient, pre-directed force is thereby exerted on the correspondingly disposed and attached orthodontic appliances, defined by the individual brackets, archwires, etc, attached to the lower canine 50' and upper molar 52', so as to correct the indicated under bite condition.

It is again emphasized that the orthodontic component 10 comprising the embodiment of the elastic module 12 is not limited to the corrective applications as represented in FIGS. 7 and 8. To the contrary the reliable and consistent structure of the orthodontic component 10 of the present invention allows its use in a myriad of applications, utilizing either conventional or customized orthodontic appliances of the general type shown. Connection of the module 10 to the appropriate orthodontic appliance is accomplished by passing or "threading" a portion of the appliance through the center of the contact portion 28 associated with the correspondingly positioned connecting assembly 20 or 22. For example, when the module 10 is attached to an archwire, as in FIGS. 7 and 8, an end portion 63 or 65, or other segment thereof, is threaded through of the center of a corresponding contact portion 28,28'. The end portion 63 or 65 is then bent or folded upon itself, or otherwise oriented, to maintain the corresponding end 14 or 16 of the module 10 in an intended position on the archwire. This type of attachment also serves to prevent or at least restrict the ability of the patient to remove the attached module 10.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. An orthodontic component structured to exert a pre-directed force within the mouth of a patient, said component comprising:
   a) a module formed of elastomeric material and having a substantially elongated configuration and a substantially uniform cross section,
   b) said module including two spaced apart ends, each end defining an oppositely disposed extremity of said module,
   c) each of said ends comprising an attachment assembly configured to engage any one of a plurality of different orthodontic appliances,
   d) each of said attachment assemblies structured to define a lasting connection to the engaged orthodontic appliance,
   e) at least one of said attachment assemblies comprising a connecting portion including an aperture extending therethrough and further comprising a contact portion disposed in overlying relation to an inner surface of said connecting portion,
   f) wherein said contact portion is formed of a hard, metallic, and substantially rigid material, and
   g) wherein said contact portion comprises a sleeve having oppositely disposed open ends fixedly inserted into said aperture.

2. An orthodontic component structured to exert a pre-directed force within the mouth of a patient, said component comprising:
   a) a module formed of elastomeric material and having a substantially elongated configuration and a substantially uniform cross section,
   b) said module including two spaced apart ends, each end defining an oppositely disposed extremity of said module,
   c) each of said ends comprising an attachment assembly configured to engage any one of a plurality of different orthodontic appliances,
   d) each of said attachment assemblies structured to define a lasting connection to the engaged orthodontic appliance,
   e) at least one of said attachment assemblies comprising a connecting portion including an aperture extending therethrough and further comprising a contact portion disposed in overlying relation to an inner surface of said connecting portion, and
   f) wherein said contact portion comprises a sleeve having oppositely disposed open ends.

3. An orthodontic component as recited in claim 2 wherein each of said attachment assemblies comprises substantially equivalent structures and corresponding dimensions.

4. An orthodontic component structured to exert a pre-directed forced on spaced apart orthodontic appliances disposed within the mouth of a patient, said component comprising:
   a) a module formed of elastomeric material, and having an elongated normally linear configuration and a substantially uniform cross section terminating in oppositely disposed ends,
   b) two attachment assemblies each secured to a different one of said ends and structured to define a lasting connection with the spaced apart orthodontic appliances,
   c) each of said attachment assemblies comprising a connecting portion and a contact portion,
   d) said connecting portion integrally secured to a corresponding one of said ends and said contact portion disposed in engagement with a corresponding one of the orthodontic appliances,
   e) wherein said connection portion comprises an aperture extending therethrough,
   f) wherein said contact portion is disposed in overlying relation to an inner surface of a corresponding one of said connecting portions, and
   g) wherein said contact portion comprises a sleeve having oppositely disposed open ends.

5. An orthodontic component as recited in claim 4 wherein each of said contact portions is formed of a metallic material.

6. An orthodontic component as recited in claim 5 wherein each of said connecting portions is formed of said elastomeric material.

7. An orthodontic component as recited in claim 4 wherein each of said contact portions is dimensioned and configured to receive a segment of the orthodontic appliance threaded therethrough.

8. An orthodontic component structured to exert a pre-directed force within the mouth of a patient, said component comprising:
   a) a module formed of elastomeric material and having a substantially elongated configuration,
   b) said module including two spaced apart ends, each end defining an oppositely disposed extremity of said module,
   c) said module including an intermediate segment having a substantially uniform cross section interconnecting said spaced apart ends,
   d) each of said ends comprising an attachment assembly configured to engage any one of a plurality of different orthodontic appliances,
   e) each of said attachment assemblies structured to define a lasting connection to the engaged orthodontic appliance,
   f) wherein at least a first portion of each of said attachment assemblies is integrally formed on said module and a second portion of each of said attachment assemblies is connected to said module, and
   g) wherein said second portion of each of said attachment assemblies is secured to a corresponding one of said first portion and is formed of a hard, substantially rigid material.

9. An orthodontic component as recited in claim 8 wherein each of said first portions is formed of said elastomeric material.

10. An orthodontic component as recited in claim 9 wherein each of said second portions is formed of a metallic material.

11. An orthodontic component as recited in claim 8 wherein each of said second portions is disposed in force bearing engagement with the engaged orthodontic appliance.

12. An orthodontic component as recited in claim 11 wherein each of said second portions is formed of a metallic material.

13. An orthodontic component as recited in claim 12 wherein each of said first portions is formed of said elastomeric material.

14. An orthodontic component as recited in claim 11 wherein said intermediate segment has a normally linear configuration.

15. An orthodontic component as recited in claim 14 wherein said intermediate segment is integrally formed to said spaced apart ends to at least partially define said module as an integral, one piece construction.

16. An orthodontic component structured to exert a pre-directed force within the mouth of a patient, said component comprising:
   a) a module formed of elastomeric material and having a substantially elongated configuration,
   b) said module including two spaced apart ends, each end defining an oppositely disposed extremity of said module,
   c) said module including an intermediate segment having a substantially uniform cross section interconnecting said spaced apart ends,
   d) each of said ends comprising an attachment assembly configured to engage any one of a plurality of different orthodontic appliances,
   e) each of said attachment assemblies structured to define a lasting connection to the engaged orthodontic appliance,
   f) wherein at least one of said attachment assemblies comprises a connecting portion including an aperture extending there through and a contact portion disposed in overlying relation to an inner surface of said connecting portion, and
   g) wherein said contact portion is formed of a hard, substantially rigid material.

17. An orthodontic component as recited in claim 16 wherein said contact portion is formed of a metallic material.

18. An orthodontic component structured to exert a pre-directed forced on spaced apart orthodontic appliances disposed within the mouth of a patient, said component comprising:
   a) a module formed of elastomeric material and having an elongated normally linear configuration and a substantially uniform cross section terminating in oppositely disposed ends,
   b) said module including an intermediate segment having a substantially uniform cross section interconnecting said ends,
   c) two attachment assemblies each secured to a different one of said ends and structured to define a lasting connection with the spaced apart orthodontic appliances.
   d) each of said attachment assemblies comprising a connecting portion and a contact portion,
   e) said connecting portion integrally secured to a corresponding one of said ends and said contact portion disposed in engagement with a corresponding one of the orthodontic appliances,
   f) wherein said connecting portion of each of said attachment assemblies comprises an aperture extending there through,
   g) wherein said contact portion of each of said attachment assemblies is disposed in overlying relation to an inner surface of said connecting portion and is formed of a hard, substantially rigid material.

19. An orthodontic component as recited in claim 18 wherein said contact portion of each of said attachment assemblies is formed of a metallic material.

* * * * *